April 26, 1966 T. H. GEWECKE Re. 26,006

TRANSFUSION SET

Original Filed Dec. 23, 1959

INVENTOR.

Theodore H. Gewecke

BY

Ralph Hammar

Attorney

United States Patent Office

Re. 26,006
Reissued Apr. 26, 1966

26,006
TRANSFUSION SET

Theodore H. Gewecke, Baldwin, Ga., assignor, by mesne assignments, to McGaw Laboratories, Inc., Milledgeville, Ga., a corporation of Delaware Original No. 3,054,401, dated Sept. 18, 1962, Ser. No. 861,658, Dec. 23, 1959. Application for reissue Sept. 15, 1964, Ser. No. 410,838
20 Claims. (Cl. 128—214)

Matter enclosed in heavy brackets [ ] appears in the original patent but forms no part of this reissue specification; matter printed in italics indicates the additions made by reissue.

This invention is an expendable transfusion set for gravity or pressure use in which the flow is easily observed in a transparent drip chamber and can be regulated from a slow drip to full flow with the drip level remaining constant at all rates of flow, even under the highest pressures.

Figure 1:
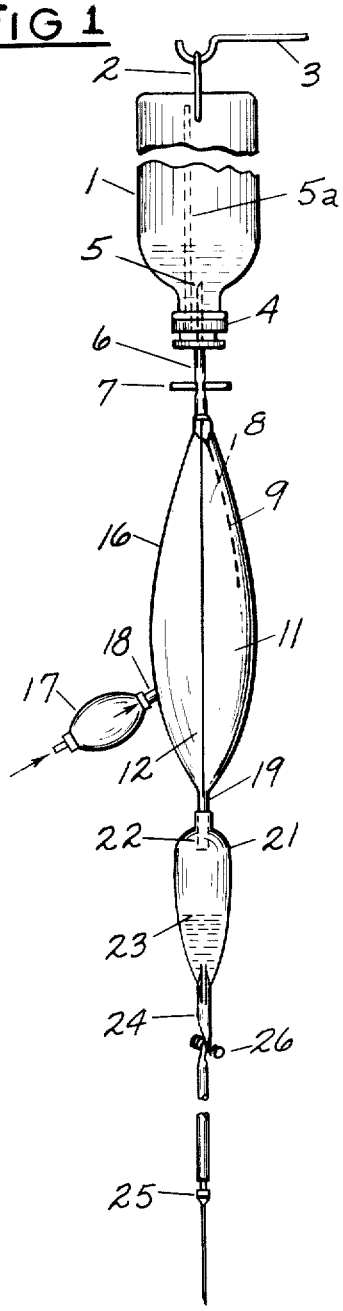
Figure 2:
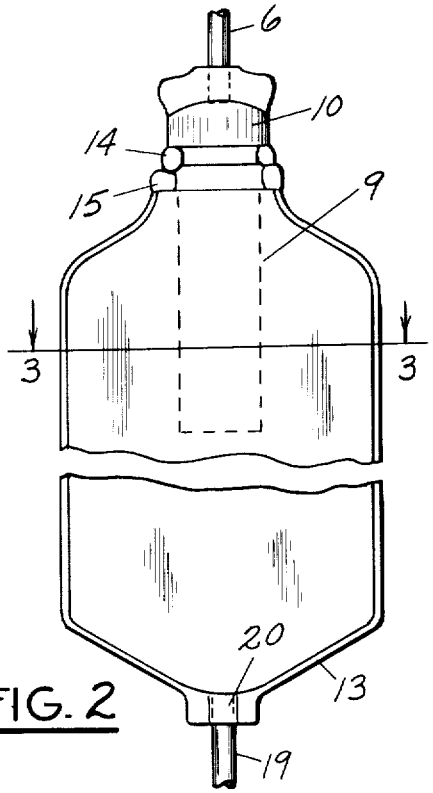
Figure 4:
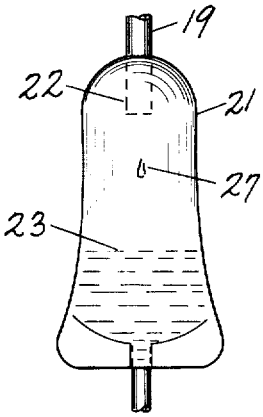
Figure 5:
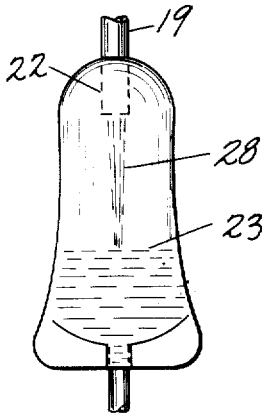
Figure 3:
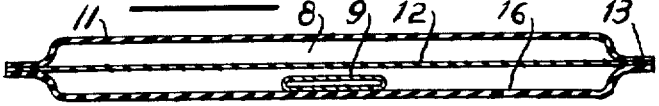

In the drawing, FIG. 1 shows the transfusion set ready for use, FIG. 2 is a front view of the combined blood and pressure chamber envelope in pre-use condition, FIG. 3 is a section on line 3—3 of FIG. 2 with the normally flat walls of the blood and pressure chambers spread apart for the purpose of illustration, FIG. 4 is a view of the drip chamber under slow drip conditions, and FIG. 5 is a similar view of the drip chamber under full flow conditions.

In the drawing, 1 indicates a blood bottle or similar container for liquid to be administered supported by a bail 2 on a hook 3 on a suitable stand. At the lower end of the bottle is a rubber stopper 4 through which is inserted the cannula 5 of a transfusion set to connect the set to the bottle. 5a is in air inlet tube. The flow of blood from the cannula is through a flexible plastic tube 6 controlled by a clamp 7.

The lower end of the tube 6 is sealed to the upper end of a plastic walled blood chamber 8 and discharges to the interior of a suitable tubular filter 9 so that all of the blood flowing into the blood chamber must pass through the filter. As shown more clearly in FIG. 2, there is a short length 10 of flexible plastic tubing heat sealed to the lower end of the tube 6 and leading to the upper end of the filter 9. The tubing 6 and 10 is transparent and when the blood chamber 8 is filled, the blood rises into the tubing 10 and blood chamber 8 may be squeezed to force air above the clamp 7, after which the tubing 6 is shut off by the clamp 7 so that there is no air within the blood chamber to cause air embolism.

The blood chamber 8 is made from two sheets 11, 12 of flexible plastic, heat sealed around the periphery as indicated at 13 and likewise heat sealed to the tube 10 at 15 and to the lower tube 19 at 20. The filter is sealed into the tube 10 at 14. On the opposite side of the sheet 12 is another sheet 16 of flexible plastic which is heat sealed around the periphery at the same time the sheets 11 and 12 are heat sealed to form the blood chamber. The space between the sheets 12 and 16 provides a pressure chamber into which air may be pumped by a squeeze bulb pump 17 attached to a nipple 18 in the sheet 16. The air pressure is applied to the blood through the flexible sheet 12 thereby developing hydraulic pressure in the blood without running the risk of air entering blood chamber 8.

At the lower end of blood chamber 8 is a draw-off tube 19 having its upper end 20 projecting slightly above the bottom wall of the blood chamber, e.g. ¼ inch. The projection 20 permits substantially complete drainage of the blood chamber. Without the projection 20, as much as from 25 to 30 cc. of blood may be trapped between the flexible walls 11 and 12 of the blood chamber no matter how much pressure is applied.

The draw-off tube is sealed to a metering device such as a plastic drip chamber 21 with its lower end 22 projecting into the chamber in the usual manner so that the blood can fall into the drip chamber in the form of drops which can be counted. In the lower end of the drip chamber, a drip level is established at 23 providing a pool of blood which drains through dispensing tubing 24 to the needle 25. The flow of blood is controlled by a regulating clamp 26 of any suitable kind, for example of the type shown in co-pending application Serial No. 789,662 filed January 28, 1959, now abandoned. When the regulating clamp 26 shuts off flow in the tube 24, no blood flows into the drip chamber. As the adjustment clamp is turned to open the tube 24, the blood flows at progressively increased rates. At slow flows, the blood flows in the form of drops as indicated at 27 in FIG. 4. At maximum flow, the blood flows in a solid stream as indicated at 28 in FIG. 5. Under all conditions, the drip level 23 remains substantially constant although under pressure, there may be a temporary slight rising of the liquid level due to compression of the air trapped in the drip chamber above the liquid level.

The transfusion set may be used for gravity feed, in which case no pressure is applied to the compression chamber. The drip level will still be as indicated at 23. However, the rates of flow usual with gravity feed are also obtainable with pressure feed with the added advantage that when pressure is applied, it is also possible to obtain quickly the higher rates of flow which are only possible with pressure.

The transfussion set is sufficiently low in cost to permit use as the standard administration set for all surgical transfusions. While pressure may not be needed, it is always instantly available should an emergency arise.

The set can be used for other liquids either separately or together with blood. When more than one unit is to be used, the pressure chamber is exhausted and the cannula 5 is removed from the stopper 4 of the preceding bottle and inserted in the stopper of a new bottle to refill the blood chamber after which the transfusion proceeds by gravity or pressure as desired. The filter 9 has capacity sufficient for the maximum number of units of blood to be given any patient at one time.

The set permits the filtration of blood to take place prior to administration without the use of additional equipment. Thus, blocking of the filter cannot occur during administration when the patient may require blood without delay. Furthermore, it eliminates the present practise of exerting gas pressure in the bottle itself where the air may enter the vein through the transfusion set of the clamp is not closed immediately after the bottle empties of blood, possibly causing death of the patient.

What is claimed as new is:

1. An expandable unitary transfusion set assembly comprising a bag having flexible plastic outer walls and an intermediate flexible plastic wall peripherally sealed to the outer walls and dividing the bag into two chambers on opposite sides of the intermediate wall and out of communication with each other, one chamber being the blood chamber and the other chamber being the pressure chamber, means for connecting the blood chamber to a blood bottle and including a shut-off, a filter within the blood chamber in the path of flow of blood from the blood bottle to the blood chamber, a drain tube permanently sealed to and leading from the lower end of the blood chamber, a drip chamber permanently sealed to and connected at its upper end to said drain tube and at its lower end to dispensing tubing, said drip chamber having a drip level above its lower end, a flow regulating clamp in the dispensing tubing, and a means for supplying fluid under pressure to said pressure chamber to force the blood out of the blood chamber at a rate controllable by said flow regulating clamp.

2. An expendable unitary transfusion set assembly comprising a bag having flexible plastic outer walls and an intermediate flexible plastic wall peripherally sealed to the outer walls and dividing the bag into two chambers on opposite sides of the intermediate wall and out of communication with each other, one chamber being the blood chamber and the other chamber being the pressure chamber, means for connecting the blood chamber to a blood bottle and including a shut-off, a filter within the blood chamber in the path of flow of blood from the blood bottle to the blood chamber, a drain tube permanently sealed to and leading from the lower end of the blood chamber, a drip chamber permanently sealed to and connected at its upper end to said drain tube and at its lower end to dispensing tubing, said drip chamber having a drip level above its lower end, a flow regulating clamp in the dispensing tubing, a squeeze bulb pressure pump, a fitting in the pressure chamber for connection to said squeeze bulb for supplying fluid under pressure to said pressure chamber to force the blood out of the blood chamber at a rate controllable by said flow regulating clamp.

3. An expendable unitary transfusion set assembly comprising a bag having flexible plastic outer walls and an intermediate flexible plastic wall dividing the bag into two chambers on opposite sides of the intermediate wall and out of communication with each other, one chamber being the blood chamber and the other chamber being the pressure chamber, means for connecting the blood chamber to a blood bottle and including a shut-off, a filter within the blood chamber in the path of flow of blood from the blood bottle to the blood chamber, a drain tube permanently sealed to and leading from the lower end of the blood chamber, the upper end of the drain tube projecting slightly above the lower end of the blood chamber, a drip chamber permanently sealed to and connected at its upper end to said drain tube and at its lower end to dispensing tubing, said drip chamber having a drip level above its lower end, a flow regulating clamp in the dispensing tubing, and a means for supplying fluid under pressure to said pressure chamber to force the blood out of the blood chamber at a rate controllable by said flow regulating clamp.

4. An expendable unitary transfusion set assembly comprising a bag having collapsible plastic outer walls and an intermediate plastic wall sandwiched between and sealed to the outer walls and dividing the bag into two chambers on opposite sides of the intermediate wall and out of communication with each other, one chamber being the blood chamber and the other chamber being the pressure chamber, a tube permanently sealed to and connected between the upper end of the blood chamber and a cannula for insertion in the stopper of a blood bottle, said tube including a shut-off, a filter within the blood chamber sealed to said tube and in the path of flow of blood from the blood bottle to the blood chamber, a drain tube permanently sealed to and leading from the lower end of the blood chamber, a drip chamber permanently sealed to and connected at its upper end to said drain tube and at its lower end to dispensing tubing, said drip chamber having a drip level above its lower end, a flow adjusting clamp in the dispensing tubing, and a means for supplying fluid under pressure to said pressure chamber to force the blood out of the blood chamber at a rate limited by said flow adjusting clamp.

5. An expendable unitary transfusion set assembly comprising a plastic bag having two collapsible chambers respectively on one and on the opposite side of a common flexible plastic wall shared by the chambers and out of communication with each other, one chamber being the blood chamber and the other chamber being the pressure chamber, means for connecting the blood chamber to a blood bottle and including a shut-off, an inlet tube and a shut-off in the tube through which the air in the blood chamber can be expelled by squeezing the chamber prior to closing the drain tube permanently sealed to and leading from the lower end of the blood chamber to dispensing tubing, flow indicating and regulating means in the dispensing tubing, and a means for supplying fluid under pressure to said pressure chamber to force the blood out of the blood chamber at a rate controllable by said flow regulating means.

6. An expendable unitary transfusion set assembly comprising a plastic bag having two collapsible chambers respectively on one and on the oppsite side of a common flexible plastic wall shared by the chambers and out of communication with each other, one chamber being the blood chamber and the other chamber being the pressure chamber, means for connecting the blood chamber to a blood bottle and including an inlet tube and a shut-off in the tube through which the air in the blood chamber can be expelled by squeezing the chamber prior to closing the shut-off, a drain tube permanently sealed to and leading from the lower end of the blood chamber, a drip chamber permanently sealed to and connected at its upper end to said drain tube and at its lower end to dispensing tubing, said drip chamber having a drip level above its lower end, a filter in the path of flow of blood to the drip chamber, a flow regulating means in the dispensing tubing, and a means for supplying fluid under pressure to said pressure chamber to force the blood out of the blood chamber at a rate controllable by said flow regulating means.

7. An expendable unitary transfusion set assembly comprising a bag having flexible plastic outer walls and an intermediate flexible plastic wall dividing the bag into two chambers on opposite sides of the intermediate wall and out of communication with each other, one chamber being the blood chamber and the other chamber being the pressure chamber, means for connecting the blood chamber to a blood bottle and including a shut-off, a filter within the blood chamber in the path of flow of blood from the blood bottle to the blood chamber, a drain tube permanently sealed to and leading from the lower end of the blood chamber, a metering device permanently sealed to and connected at its upper end to said drain tube and at its lower end to dispensing tubing, a flow regulating clamp in the dispensing tubing, and a means for supplying fluid under pressure to said pressure chamber to force the blood out of the blood chamber at a rate controllable by said flow regulating clamp.

8. An expendable unitary transfusion set assembly comprising a bag having flexible plastic outer walls and an intermediate flexible plastic wall dividing the bag into two chambers on opposite sides of the intermediate wall and out of communication with each other, one chamber being the blood chamber and the other chamber being the pressure chamber, means for connecting the blood chamber to a blood bottle and including a shut-off, a filter within the blood chamber in the path of flow of blood from the blood bottle to the blood chamber, a drain tube permanently sealed to and leading from the lower end of the blood chamber to dispensing tubing, a flow regulating device in the dispensing tubing, and a means for supplying fluid under pressure to said pressure chamber to force the blood out of the blood chamber at a rate controllable by said flow regulating device.

9. An expendable unitary transfusion set assembly comprising a bag having collapsible plastic outer walls and an intermediate plastic wall sandwiched between and sealed to the outer walls and dividing the bag into two chambers on opposite sides of the intermediate wall and out of communication with each other, one chamber being the blood chamber and the other chamber being the pressure chamber, a tube permanently sealed to and connected between the upper end of the blood chamber and a cannula for insertion in the stopper of a blood bottle, said tube including a shut-off, a filter within the blood chamber in the path of flow of blood from the blood bottle to the blood chamber, a drain tube permanently sealed to and leading from the lower end of the blood chamber to dispensing tubing, a flow adjusting means in the dispensing tubing, and a means for supplying fluid under pressure to said pressure chamber to force the blood out of the blood chamber at a rate limited by said flow adjusting means.

10. An expendable unitary transfusion set assembly comprising a plastic bag having two collapsible chambers respectively on one and on the opposite side of a common flexible plastic wall shared by the chambers and out of communication with each other, one chamber being the blood chamber and the other chamber being the pressure chamber, means for connecting the blood chamber to a blood bottle and including an inlet tube and a shut-off in the tube through which the air in the blood chamber can be expelled by squeezing the chamber prior to closing the shut-off, a drain tube permanently sealed to and leading from the lower end of the blood chamber, a flow indicator permanently sealed to and connected at its upper end to said drain tube and at its lower end to dispensing tubing, a filter in the path of flow of blood to the flow indicator, a flow regulating means in the dispensing tubing, and a means for supplying fluid under pressure to said pressure chamber to force the blood out of the blood chamber at a rate controllable by said flow regulating means.

11. A unitary transfusion set assembly comprising a bag having collapsible outer walls and an intermediate wall sandwiched between and sealed to the outer walls and dividing the bag into two chambers respectively on one and on the opposite side of the intermediate wall and out of communication with each other, one chamber being the blood chamber and the other chamber being the pressure chamber, a cannula for insertion in the stopper of a blood bottle, a tube having its upper end connected to said cannula, a shut off clamp on said tube, a tubular filter having a closed lower end within the blood chamber and having an open upper end, means sealing the open upper end of the filter to the lower end of said tube whereby blood flowing from the tube into the blood chamber flows through said filter, a drain tube leading from the lower end of the blood chamber, a drip chamber connected at its upper end to said drain tube and at its lower end to dispensing tubing, said drip chamber having a drip level above its lower end, a flow adjusting clamp in the dispensing tubing, and a means for supplying fluid under pressure to said pressure chamber to force the blood out of the blood chamber at a rate limited by said flow adjusting clamp.

12. A unitary transfusion set assembly comprising a bag having collapsible outer walls and an intermediate wall sandwiched between and sealed to the outer walls and dividing the bag into two chambers respectively on one and on the opposite side of the intermediate wall and out of communication with each other, one chamber being the blood chamber and the other chamber being the pressure chamber, a cannula for insertion in the stopper of a blood bottle, a tube having its upper end connected to said cannula, a shut off clamp on said tube, a tubular filter having a closed lower end within the blood chamber and having an open upper end, means sealing the open upper end of the filter to the lower end of said tube whereby blood flowing from the tube into the blood chamber flows through said filter, a drain tube leading from the lower end of the blood chamber to dispensing tubing, a flow adjusting means in the dispensing tubing, and a means for supplying fluid under pressure to said pressure chamber to force the blood out of the blood chamber at a rate limited by said flow adjusting means.

13. A unitary transfusion set assembly comprising a bag having flexible outer walls and an intermediate flexible wall peripherally sealed to the outer walls and dividing the bag into two chambers respectively on one and on the opposite side of the intermediate wall and out of communication with each other, one chamber being the blood chamber and the other chamber being the pressure chamber, a tube having at its upper end means for connecting to a bood bottle, a shut off clamp on said tube, a tubular filter having a closed lower end within the blood chamber and having an open upper end, means sealing the open upper end of the filter to the lower end of said tube whereby blood flowing from the tube into the blood chamber flows through said filter, a drain tube leading from the lower end of the blood chamber, a drip chamber connected at its upper end to said drain tube and at its lower end to dispensing tubing, said drip chamber having a drip level above its lower end, a flow regulating clamp in the dispensing tubing, a squeeze bulb pressure pump, a fitting in the pressure chamber for connection to said squeeze bulb and supplying fluid under pressure to said pressure chamber to force the blood out of the blood chamber at a rate controllable by said flow regulating clamp.

14. A unitary transfusion set assembly comprising a bag having flexible outer walls and an intermediate flexible wall dividing the bag into two chambers respectively on one and on the opposite side of the intermediate wall and out of communication with each other, one chamber being the blood chamber and the other chamber being the pressure chamber, a tube having at its upper end means for connecting to a blood bottle, a shut off clamp on said tube, a tubular filter having a closed lower end within the blood chamber and having an open upper end, means sealing the open upper end of the filter to the lower end of said tube whereby blood flowing from the tube into the blood chamber flows through said filter, a drain tube leading from the lower end of the blood chamber, the upper end of the drain tube projecting slightly above the lower end of the blood chamber, a drip chamber connected at its upper end to said drain tube and at its lower end to dispensing tubing, said drip chamber having a drip level above its lower end, a flow regulating clamp in the dispensing tubing, and a means for supplying fluid under pressure to said pressure chamber to force the blood out of the blood chamber at a rate controllable by said flow regulating clamp.

15. A unitary transfusion set assembly comprising a bag having flexible outer walls and an intermediate flexible wall dividing the bag into two chambers respectively on one and on the opposite side of the intermediate wall and out of communication with each other, one chamber being the blood chamber and the other chamber being the pressure chamber, a tube having at its upper end means for connecting to a blood bottle, a shut off clamp on said tube, a tubular filter having a closed lower end within the blood chamber and having an open upper end, means sealing the open upper end of the filter to the lower end of said tube whereby blood flowing from the tube into the blood chamber flows through said filter, a drain tube leading from the lower end of the blood chamber, a metering device connected at its upper end to said drain tube and at its lower end to dispensing tubing, a flow regulating claim pin the dispensing tubing, and a means for supplying fluid under pressure to said pressure chamber to force the blood out of the blood chamber at a rate controllable by said flow regulating clamp.

16. A unitary transfusion set assembly comprising a bag having two collapsible chambers respectively on one and on the opposite side of a common flexible plastic wall shared by the chambers and out of communication with each other, one chamber being the blood chamber and the other chamber being the pressure chamber, a tube having at its upper end means for connecting to a blood bottle, a shut off clamp on said tube, said tube having its lower end sealed to said blood chamber, a drain tube leading from the lower end of the blood chamber to dispensing tubing, flow indicating and regulating means in the dispensing tubing, and a means for supplying fluid under pressure to said pressure chamber to force the blood out of the blood chamber at a rate controllable by said flow regulating means.

17. In an administration set, a blood bag having spaced flexible plastic walls, a plastic inlet tube having one end entering and sealed to the bag, [a shut-off in the tube] *said tube having associated shut-off means* through which air may be expelled by squeezing the bag prior to closing the shut-off, an outlet from the bag for conducting blood to a patient, another wall outside and sealed at its edges to one of the walls of the bag and forming therewith a pressure chamber external to the bag, and a pressure pump connected to said other wall for developing a pressure on said one wall of the bag forcing blood under pressure out through said outlet.

18. The administration set of claim 17 having in addition a filter within the blood bag sealed to the entering end of the inlet tube.

19. The administration set of claim 17 in which the bag and pressure chamber comprise three sheets of flexible plastic arranged one on top of the other and sealed to each other around the peripheral edges, one of the outer sheets and the intermediate sheet comprising the blood bag, and the other of the outer sheets and the intermediate sheet comprising the pressure chamber.

20. The administration set of claim 17 in which the outlet comprises a plastic tube with one end entering and sealed to the bottom of the blood bag and projecting slightly above the bottom of the blood bag.

References Cited by the Examiner

The following references, cited by the Examiner, are of record in the patented file of this patent or the original patent.

UNITED STATES PATENTS

| | | | |
|---|---|---|---|
| 972,201 | 10/1910 | Kassart | 128—227 |
| 1,205,410 | 11/1916 | Tenny | 128—214 |
| 2,231,418 | 2/1941 | Trotter | 128—214 |
| 2,409,734 | 10/1946 | Bucher | 128—214 |
| 2,702,034 | 2/1955 | Walter | 128—214 |
| 2,766,907 | 10/1956 | Wallace | 128—214 X |
| 2,848,995 | 8/1958 | Ryan | 128—214 |
| 2,907,325 | 10/1959 | Burke | 128—214 |
| 2,915,063 | 12/1959 | Cutter | 128—214 |

FOREIGN PATENTS

| | | |
|---|---|---|
| 321,359 | 6/1957 | Switzerland. |

OTHER REFERENCES

Walter et al.: "A Closed Gravity Technique for the Preservation of Whole Blood in ACD Solution Utilizing Plastic Equipment," from Surgery, Gyne. and Obstet., vol. 94, #6, June 52, pages 687–692.

RICHARD A. GAUDET, *Primary Examiner.*